United States Patent [19]
Fulton

[11] Patent Number: 5,287,865
[45] Date of Patent: Feb. 22, 1994

[54] DENTAL FLOSSER APPARATUS

[76] Inventor: Jesse O. Fulton, 109 Springridge Dr., Vicksburg, Miss. 39180

[21] Appl. No.: 44,759

[22] Filed: Apr. 12, 1993

[51] Int. Cl.$^5$ .............................................. A61C 15/00
[52] U.S. Cl. ................................... 132/323; 132/325; 132/326
[58] Field of Search ............... 132/323, 324, 325, 326, 132/327

[56] References Cited

U.S. PATENT DOCUMENTS

| | | | |
|---|---|---|---|
| 2,163,500 | 6/1939 | Shepard | 132/326 |
| 2,217,917 | 10/1940 | Munro | 132/326 |
| 3,792,706 | 2/1974 | Keese | 132/324 |
| 3,993,085 | 11/1975 | Skinner | 132/325 |
| 4,094,328 | 6/1978 | Ray | 132/325 |
| 4,508,125 | 4/1985 | Loubier | 132/326 |
| 4,671,307 | 6/1987 | Curbow et al. | 132/323 |
| 4,691,719 | 9/1987 | Ciccarelli | 132/325 |
| 5,020,554 | 6/1991 | Feinberg | 132/324 |
| 5,176,157 | 1/1993 | Mazza | 132/325 |
| 5,186,191 | 2/1993 | Loubier | 132/325 |

FOREIGN PATENT DOCUMENTS 0330116  6/1903  France ............................ 132/325

Primary Examiner—Gene Mancene
Assistant Examiner—Frank A. LaViola
Attorney, Agent, or Firm—Leon Gilden

[57] ABSTRACT

A dental floss applicator structure is arranged to include a framework to mount a dental floss dispenser housing, wherein the housing directs a dental floss filament from the housing about a smooth groove, that in turn directs the filament through a first guide post and through spaced first and second extension legs directing the filament between the extension legs and returning the filament through a second guide post and wrapped around the guide post below the framework as a take-up structure.

2 Claims, 4 Drawing Sheets

DENTAL FLOSSER APPARATUS

BACKGROUND OF THE INVENTION

1. Field of the Invention

The field of invention relates to dental floss applicator and dispensing apparatus, and more particularly pertains to a new and improved dental flosser apparatus wherein the same is directed to the dispensing and employment of dental floss in a dental cleaning procedure.

2. Description of the Prior Art

Dental floss holder and dispenser structure is indicated in the prior art in U.S. Pat. Nos. 4,031,999; 3,525,462; 5,038,806; 5,020,554; and 3,519,004.

The instant invention attempts to overcome deficiencies of the prior art by employing a dental floss applicator structure arranged to permit the application of dental floss to an individual's teeth permitting access to remote portions of the individual's teeth and in this respect, the present invention substantially fulfills this need.

SUMMARY OF THE INVENTION

In view of the foregoing disadvantages inherent in the known types of dental floss application structure now present in the prior art, the present invention provides a dental flosser apparatus wherein the same is directed to the application of dental floss to remote portions of an individual's teeth during a flossing procedure. As such, the general purpose of the present invention, which will be described subsequently in greater detail, is to provide a new and improved dental flosser apparatus which has all the advantages of the prior art dental floss application apparatus and none of the disadvantages.

To attain this, the present invention provides a dental floss applicator structure arranged to include a framework to mount a dental floss dispenser housing, wherein the housing directs a dental floss filament from the housing about a smooth groove, that in turn directs the filament through a first guide post and through spaced first and second extension legs directing the filament between the extension legs and returning the filament through a second guide post and wrapped around the guide post below the framework as a take-up structure.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved dental flosser apparatus which has all the advantages of the prior art dental floss application apparatus and none of the disadvantages.

It is another object of the present invention to provide a new and improved dental flosser apparatus which may be easily and efficiently manufactured and marketed.

It is a further object of the present invention to provide a new and improved dental flosser apparatus which is of a durable and reliable construction.

An even further object of the present invention is to provide a new and improved dental flosser apparatus which is susceptible of a low cost of manufacture with regard to both materials and labor, and which accordingly is then susceptible of low prices of sale to the consuming public, thereby making such dental flosser apparatus economically available to the buying public.

Still yet another object of the present invention is to provide a new and improved dental flosser apparatus which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
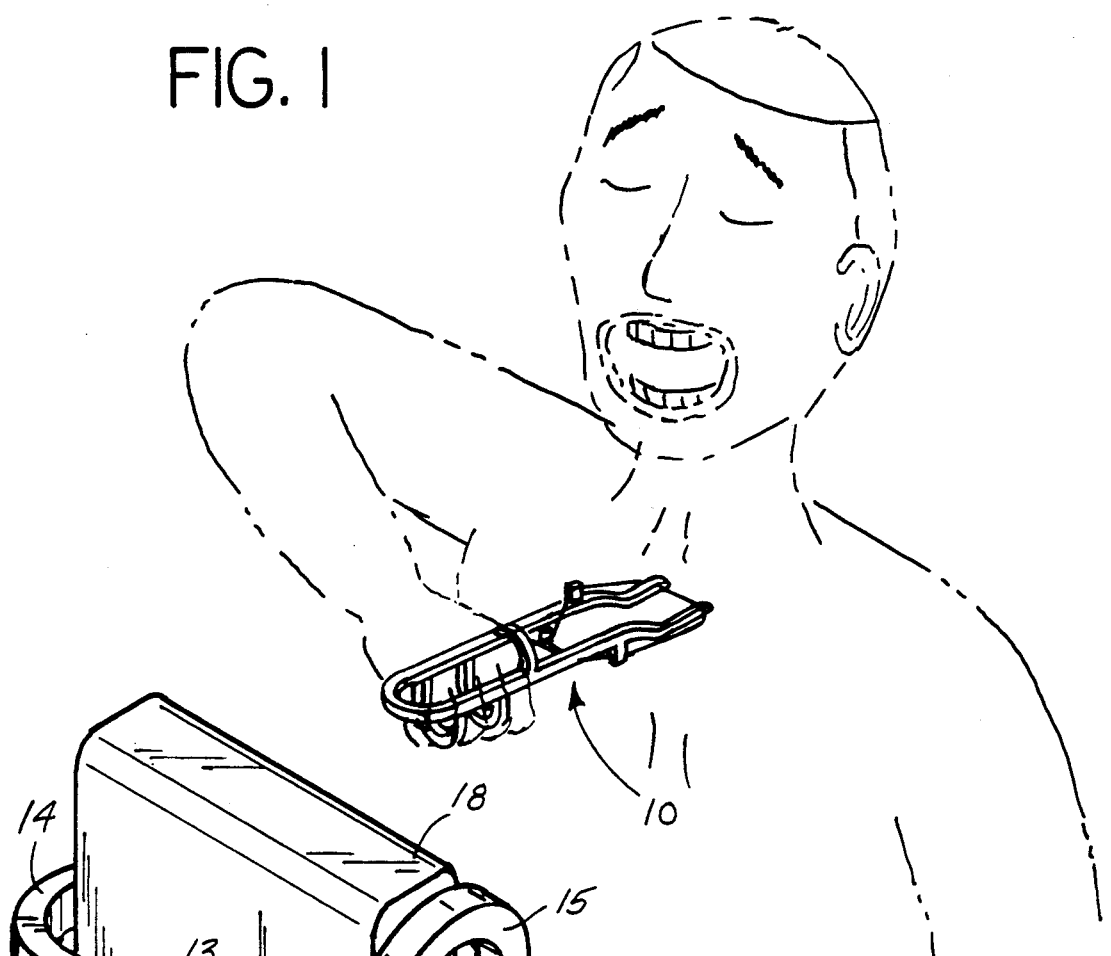
FIG. 1 is an isometric illustration of the invention in use.

With reference now to the drawings, and in particular to FIGS. 1 to 8 thereof, a new and improved dental flosser apparatus embodying the principles and concepts of the present invention and generally designated by the reference numerals 10 and 10a will be described.

Figure 2:
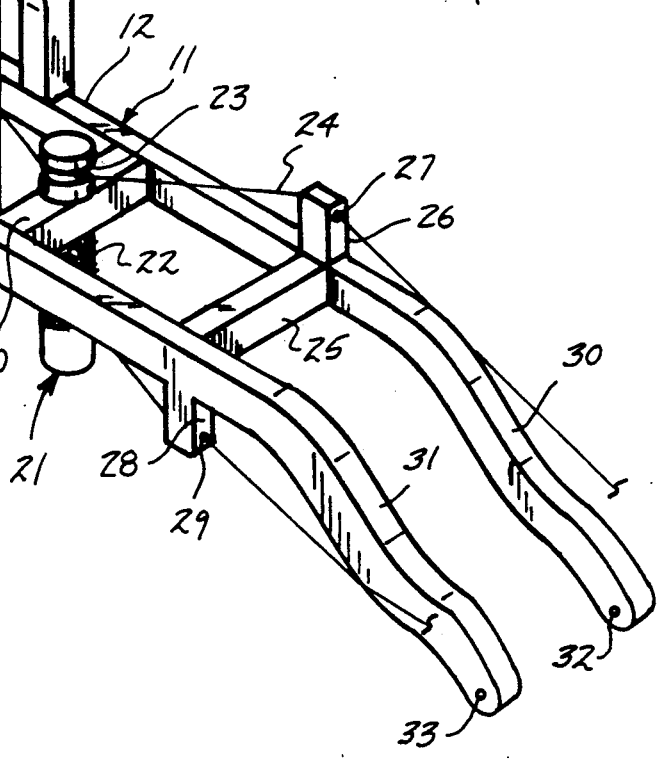
FIG. 2 is an enlarged isometric illustration of the invention.
Figure 3:
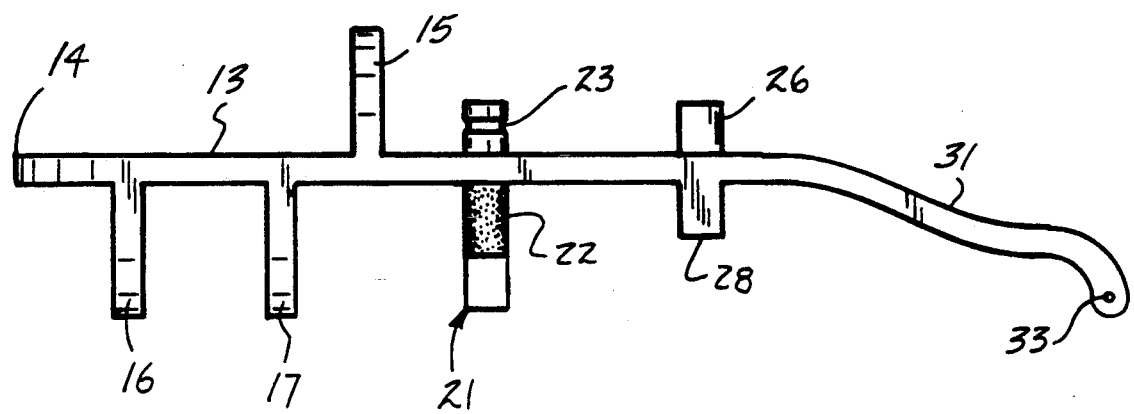
FIG. 3 is an orthographic side view of the invention.
Figure 4:
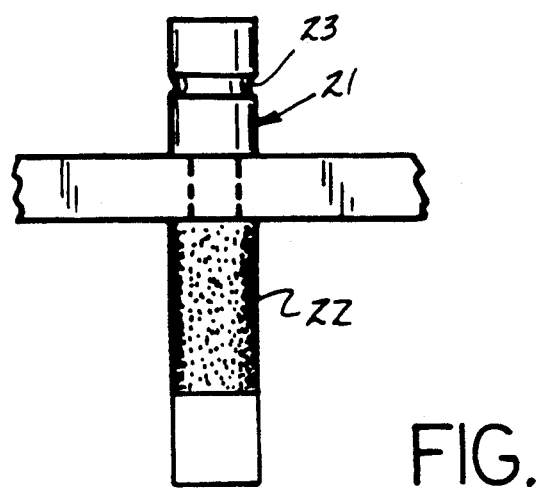
FIG. 4 is an enlarged orthographic view of the guide post structure of the invention.

More specifically, the dental flosser apparatus 10 of the instant invention essentially comprises a generally U-shaped frame portion 11, having respective first and second parallel and coextensive legs 12 and 13 respectively extending from a frame base 14, wherein an arcuate abutment bar 15 is orthogonally mounted to the first and second legs 12 and 13 extending above the first and second legs in an orthogonal relationship. Respective first and second U-shaped cradle bars 16 and 17 extend below the U-shaped frame portion 11 between the frame portion base 14 and the arcuate abutment bar 15 to receive and secure a floss dispenser housing 18 within the first and second U-shaped cradle bars 16 and 17 that is arranged to extend above and below the U-shaped frame portion 11 for abutment with the abutment bar 15, wherein an outlet opening 19 directs a dental floss filament 24 through the arcuate abutment bar 15, in a manner as illustrated in FIG. 2 for example. A first cross bar 20 extends orthogonally between the first and second legs 12 and 13 beyond the floss dispenser housing 18 and the abutment bar 15, with a rotary guide post 21 rotatably and orthogonally directed through the first cross bar 20, having a knurled cylindrical wall portion 22 oriented below the first cross bar 20 and an annular groove 23 received within an uppermost portion of the rotary guide post 21 to direct and receive the filament 24 therewithin, with a second cross bar 25 spaced from and parallel the first cross bar extending orthogonally between the first and second legs 12 and 13 to provide and impart geometric integrity to the organization, as a first guide post 26 extends orthogonally above the first leg 12 at its intersection with the second cross bar 25, and a second guide post 28 extends orthogonally below the second leg 13 at its intersection with the second cross bar 25. The first guide post 26 includes a first boer 27, with the second guide post 28 having a second bore 29, with the first and second bores 27 and 29 arranged in a parallel spaced relationship relative to one another to receive the filament therethrough as the first bore 27 receives the filament from the annular groove 23, as indicated in FIG. 2 for example. Respective first and second extension legs 30 and 31 are arranged to project colinearly from the first and second legs 12 and 13 and project below the first and second legs 12 and 13, with the first extension leg 30 having a first extension leg aperture, and the second extension leg 31 having a second extension leg aperture, with the first and second apertures oriented orthogonally relative to the first and second bores 27 and 29. In this manner, the filament is directed from the first bore 27 through the first and second apertures 32 and 33 and then is directed through the second bore 29 to be wound about the knurled cylindrical wall portion 22 as a take-up roll to receive and direct the dental floss filament thereabout as it is taken up from the dispenser housing 18.

Figure 5:
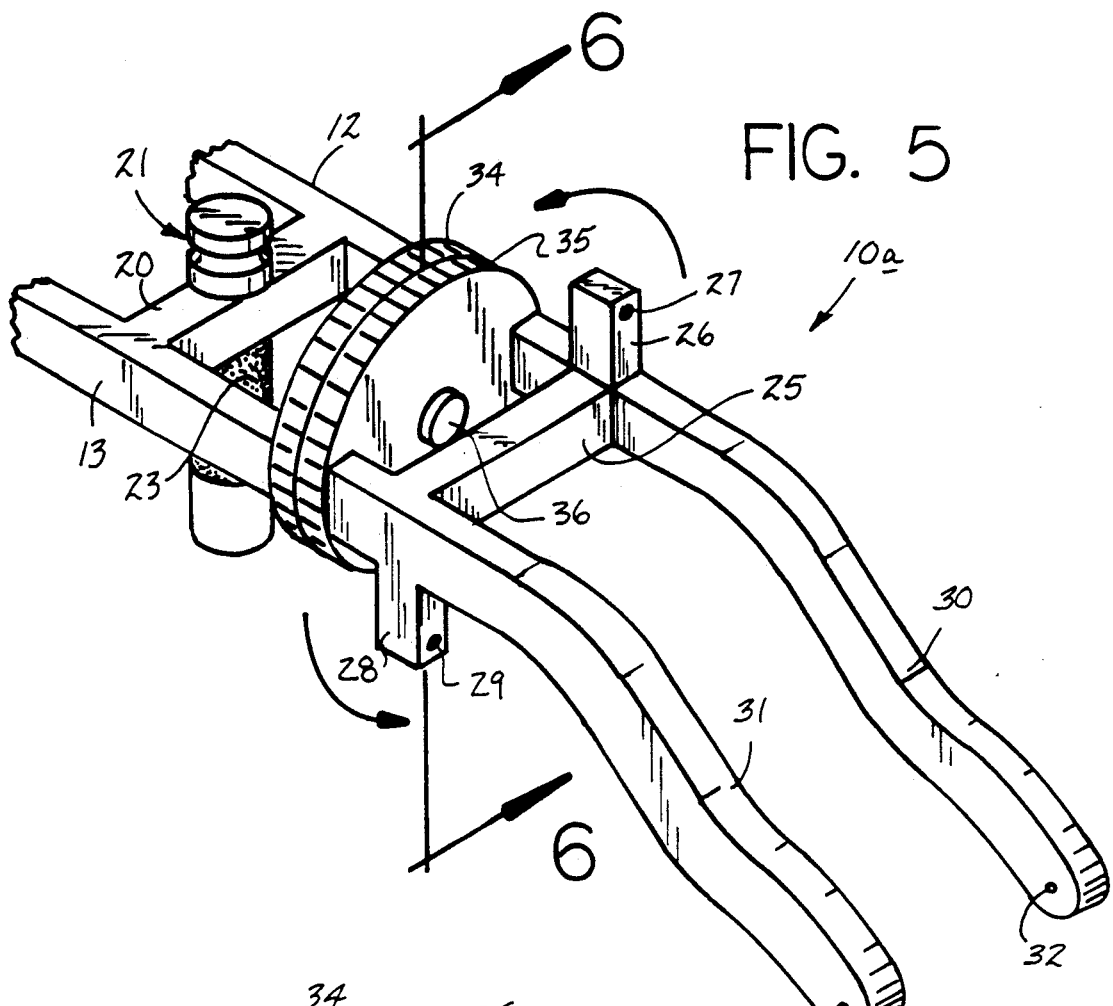
FIG. 5 is an isometric illustration of a modified aspect of the invention.
Figure 6:
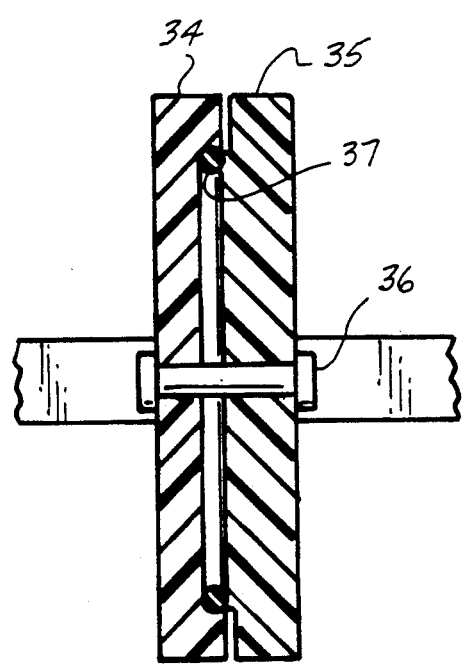
FIG. 6 is an orthographic view, taken along the lines 6—6 of FIG. 5 in the direction indicated by the arrows.

The FIGS. 5 and 6 indicate a modified apparatus 10a, wherein the first and second legs 12 and 13 are discontinuous, with a first disc 34 fixedly mounted in an orthogonal relationship relative to the first and second legs between the first and second cross bars 20 and 25, with the use of a second disc 35 fixedly and orthogonally mounted to the first and second legs 12 and 13 in adjacency to the second cross bar 25, as the first disc 34 is oriented in facing relationship relative to the first cross bar 20 such that a disc axle 36 rotatably secures the first and second discs 34 and 35 together maintaining the first and second discs in any desired angular orientation relative to one another by a disc friction ring 37 (see FIG. 6) interposed between the first and second discs 34 and 35, as indicated in FIG. 6.

Figure 7:
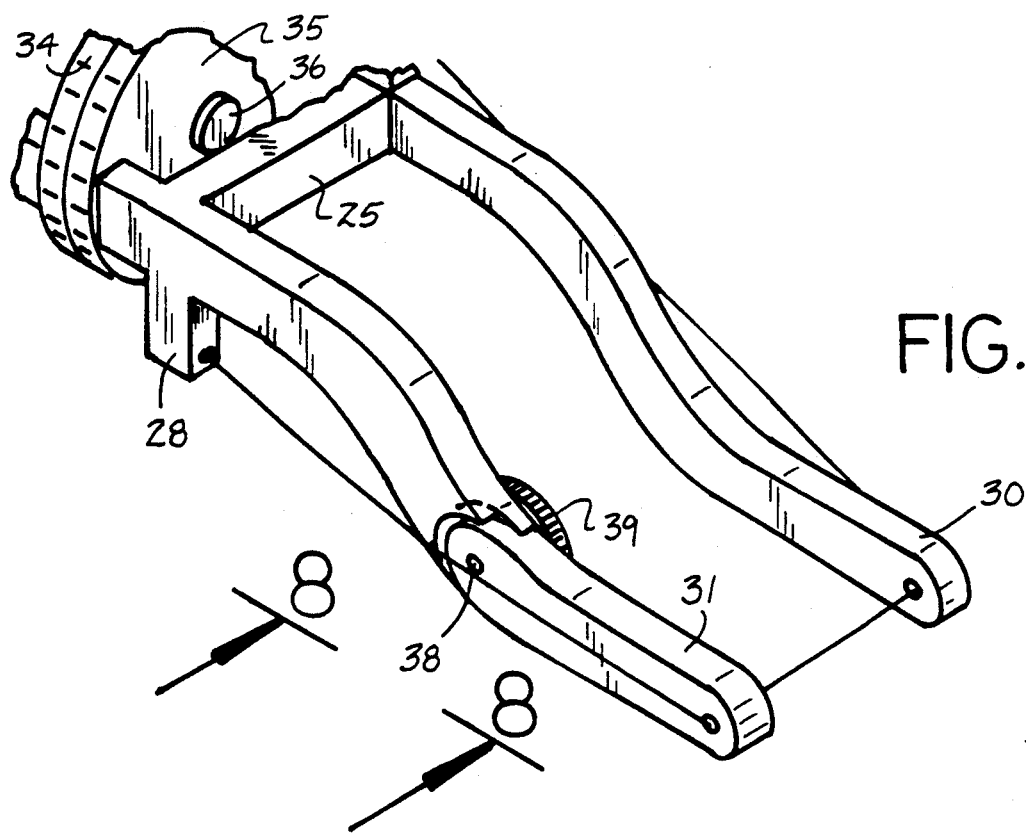
FIG. 7 is an isometric illustration of a further modified aspect of the invention employing a pivotal second extension leg.
Figure 8:
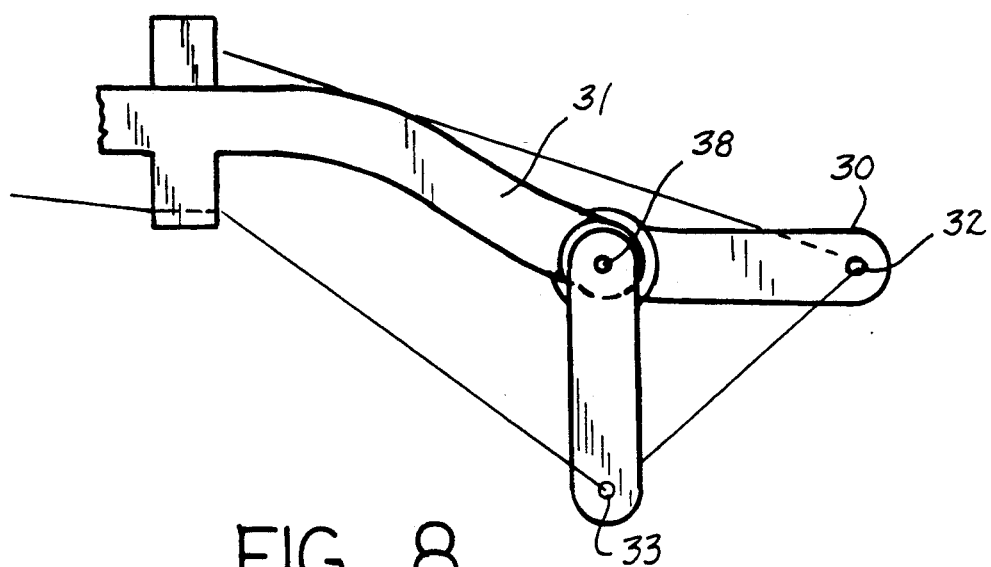
FIG. 8 is an orthographic side view of the pivotal extension leg in a displaced orientation.

The FIGS. 7 and 8 indicate a further modification of the second extension leg 31, wherein a second extension leg pivot axle joint 38 includes an axle wheel 39 to permit rotation and displacement of the second aperture 33 relative to the first aperture 32 for providing enhanced adaptability of the structure in a dental flossing procedure.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A dental flosser apparatus, comprising,
   a U-shaped frame portion, having first and second legs arranged in a parallel coextensive relationship, with the U-shaped frame portion including a frame portion base at a U-shaped frame portion first end;
   an arcuate abutment bar fixedly and orthogonally mounted to the first leg and the second leg extending above the U-shaped frame portion;
   a first and second U-shaped cradle bar oriented between the arcuate abutment bar and the U-shaped frame portion, wherein the first and second U-shaped cradle bar is directed orthogonally and below the U-shaped frame portion;
   a floss dispenser housing mounted between the first leg and the second leg and between the arcuate abutment bar and the frame portion base, with the floss dispenser housing received onto the first U-shaped cradle bar and the second U-shaped cradle bar;
   the floss dispenser housing including an outlet opening to direct a dental floss filament therefrom through the arcuate abutment bar;
   the first leg having a first extension leg extending from the first leg, and the second leg having a second extension leg extending from the second leg, with the first extension leg and the second extension leg arranged in a parallel relationship relative to one another, and the first extension leg including a first leg aperture, the second extension leg including a second leg aperture, wherein the dental floss filament is directed through the first aperture and the second aperture;

a first cross bar orthogonally directed between the first leg and the second leg, and a second cross bar arranged parallel to and spaced relative to the first cross bar orthogonally directed between the first leg and the second leg, wherein a first guide post is orthogonally mounted to the first leg at the second cross bar extending above the first leg, and a second guide post is fixedly and orthogonally mounted to the second leg extending below the second leg, wherein the first guide post includes a first bore receiving a filament therethrough, and the first bore is orthogonally oriented relative to the first aperture and the second aperture, and the second guide post having a second bore, with the second bore receiving the dental floss filament therethrough, and the second bore is oriented substantially parallel relative to the first bore;

the first cross bar includes a rotary guide post rotatably directed through the first cross bar in an orthogonal relationship, wherein the rotary guide post extends above the first cross bar, having an annular groove receiving the dental floss filament therealong for guidance, and wherein the rotary guide post extending below the first cross bar includes a knurled outer surface receiving a free distal end of the dental floss filament thereabout for winding the dental floss filament about the knurled cylindrical wall portion for winding the dental filament thereabout;

the first leg and the second leg are discontinuous between the first cross bar and the second cross bar, and a first annular disc mounted to the first leg and the second leg in a facing relationship relative to the first cross bar, and a second disc fixedly and orthogonally mounted to the first leg and the second leg in a facing relationship relative to the second cross bar, wherein a disc axle rotatably mounts the first disc to the second disc, and a disc friction ring interposed between the first disc and the second disc to maintain the first disc and the second disc in an angular predetermined orientation relative to one another.

2. An apparatus as set forth in claim 1 wherein the second extension leg includes a second extension leg pivot axle joint, and the second extension leg pivot axle joint is positioned intermediate the second extension leg and includes an axle wheel, whereupon rotation of the axle wheel rotatably displaces the second aperture relative to the first aperture.

* * * * *